(12) United States Patent
Kutushov

(10) Patent No.: US 7,601,133 B2
(45) Date of Patent: Oct. 13, 2009

(54) SYSTEM FOR CORRECTING BIOLOGICAL FLUID

(75) Inventor: Mikhail Vladimirovich Kutushov, Onezhskaya, 53-3-387, 125414 Moscow, ul. (RU)

(73) Assignees: Evgeny Pavlovich Germanov, Moscow (RU); Mikhail Vladimirovich Kutushov, Moscow (RU)

( * ) Notice: Subject to any disclaimer, the term of this patent is extended or adjusted under 35 U.S.C. 154(b) by 152 days.

(21) Appl. No.: 10/576,039

(22) PCT Filed: Sep. 20, 2004

(86) PCT No.: PCT/RU2004/000367

§ 371 (c)(1),
(2), (4) Date: Apr. 14, 2006

(87) PCT Pub. No.: WO2005/035024

PCT Pub. Date: Apr. 21, 2005

(65) Prior Publication Data

US 2007/0075008 A1   Apr. 5, 2007

(30) Foreign Application Priority Data

Oct. 14, 2003   (RU) ............................. 2003130214

(51) Int. Cl.
| | |
|---|---|
| *A61M 37/00* | (2006.01) |
| *C02F 1/44* | (2006.01) |
| *B01D 39/00* | (2006.01) |
| *B01D 35/06* | (2006.01) |
| *C02F 1/48* | (2006.01) |

(52) U.S. Cl. .................. 604/6.08; 604/4.01; 604/5.04; 604/6.09; 210/645; 210/222; 210/223; 210/502.1

(58) Field of Classification Search ................. 604/4.01, 604/5.01, 5.04, 6.08, 6.09, 6.1, 6.11; 422/44; 210/645, 222, 223, 502.1; 417/472, 473
See application file for complete search history.

(56) References Cited

U.S. PATENT DOCUMENTS

| 77,661 | A | * | 5/1868 | Schatz | ..................... 417/473 |
| 4,750,868 | A | * | 6/1988 | Lundback | ................... 417/257 |
| 5,073,094 | A | * | 12/1991 | Dorman et al. | ............. 417/412 |

(Continued)

FOREIGN PATENT DOCUMENTS

DE   10062833   6/2002

(Continued)

*Primary Examiner*—Leslie R Deak
(74) *Attorney, Agent, or Firm*—Pauley Petersen & Erickson

(57) ABSTRACT

Biology and medicine for cleaning biological fluids. A system for correcting a biological fluid includes a sealed container for a magnetically operated absorbent (MOA), a sealed chamber for mixing the absorbent with a biological fluid and for the absorbent precipitation therefrom, and a sealed filtering unit. The chamber and container are embodied so that they can modify the volumes thereof, have a common interchamber partition-wall fixed to the bottom and are interconnected through a passage embodied in the wall. The other sidewalls of the chambers have corrugations which form bellows. Lids of the chambers are pivotally connected so that they are pivotable around the pivot axis. The MOA container is arranged inside the absorber-mixing chamber and embodied as a bellow. An inlet connection is simultaneously connected to the inside cavities of the absorber-mixing chamber and to the container thereof.

31 Claims, 3 Drawing Sheets

U.S. PATENT DOCUMENTS

| | | | |
|---|---|---|---|
| 5,123,901 A * | 6/1992 | Carew | 604/5.02 |
| 5,609,572 A * | 3/1997 | Lang | 604/22 |
| 5,934,888 A * | 8/1999 | Marka et al. | 417/473 |
| 5,980,479 A | 11/1999 | Kutushov | |
| 6,036,857 A * | 3/2000 | Chen et al. | 210/222 |
| 6,616,623 B1 | 9/2003 | Kutushov | |

FOREIGN PATENT DOCUMENTS

| | | |
|---|---|---|
| RU | 1836105 | 8/1993 |
| RU | 1430 | 1/1996 |
| WO | WO 94/21310 | 9/1994 |
| WO | WO 01/24850 | 4/2001 |

* cited by examiner

SYSTEM FOR CORRECTING BIOLOGICAL FLUID

BACKGROUND OF THE INVENTION

1. Field of the Invention

This invention relates to biology and medicine and can be applied for biological fluids purification and to normalize a condition of those to physiological standards.

2. Discussion of Related Art

A facility for biological fluids correction is taught by PCT International Application PCT/RU94/00022, including a biological fluid mixing compartment or mixing chamber with a ferreed sorbent being in e.g. a physiological solution. A compartment for precipitation of the ferreed sorbent out of the biological fluid using magnets after their, the fluid and the ferreed sorbent, interaction, such as a precipitation chamber, a vessel for the ferreed sorbent with the physiological solution, and a driving gear ensuring the facility operation. The mixing chamber is connected with the vessel and the precipitation chamber by channels through a filtering device connected to the correction facility outlet socket, by an inlet socket linked to a biological fluid inflow source, e.g. to a patient's vein. Here, the inlet socket is connected with the mixing chamber through a channel, while the vessel outlet channel is input into the same channel, and valves enabling the biological fluid to flow from the inlet socket to the outlet socket of the facility are installed in the channels.

The known equipment enables biological fluids correction through removal of e.g. low-molecular and medium-molecular toxins, however, the known equipment application requires immixture of the fluid being corrected with physiological solution, as well as infusion into the biological fluid (e.g. into blood) of anticoagulants, which is not always indicated for the patient. Besides, constructive performance of the equipment is quite sophisticated.

One analogous prototype equipment is the biological fluids correction system taught by U.S. Pat. No. 5,980,479, containing a hermetical mixing chamber, a precipitation chamber and a vessel for the ferreed sorbent. The mixing compartment is connected via hose channels with the vessel and the correction chamber through a filtering device connected to the correction system outlet socket, by an inlet socket linked to the biological fluid inflow source, e.g. to a patient's vein. Biological fluid flow from the inlet socket to the outlet socket of the system is ensured by the pumps installed on the channels. The inlet socket is connected with the mixing chamber via a channel and the vessel outlet channel is input in the same channel. Also, valves controlling the biological fluid specified flow direction are installed in the channels, and the vessel has a device for maintaining the predetermined pressure.

Such system enables the possibility of biological fluid correction, however, it does also have the same disadvantages of the previously described equipment, and in order to avoid any ingress of air into the biological fluid being corrected, which air is used for e.g. maintaining the predetermined pressure in the vessel with ferreed sorbent in physiological solution, the system construction is substantially complicated, e.g. the device filtering the already processed fluid before getting out of the system is overly sophisticated.

SUMMARY OF THE INVENTION

One object of this invention is to develop a technical solution to perform a biological fluid purification at a minimal input of foreign (extraneous) reagents into the fluid being corrected.

The above and other objects are achieved with a biological fluid correction system having hermetic parts, connected via channels with valves installed in the channels for providing flow of the biological fluid through the system from the inlet socket to the outlet socket. A vessel is for the ferreed sorbent, chambers are for mixing of the ferreed sorbent with the biological fluid and precipitation of the ferreed sorbent out of the fluid, and there is a filtering device connected through the system outlet channel with the outlet socket, linked to the system inlet channel. The mixing chamber, the ferreed sorbent precipitation chamber and the vessel for ferreed sorbent have an ability to change their volumes and have a corresponding driving gear. Here, the chambers for mixing of the ferreed sorbent with the biological fluid and for the ferreed sorbent precipitation out of the biological fluid are made in the form of vessels having either rigidly connected covers, or one common lid, as well as one common wall mounted to the bottom of the chambers and are made as an interchamber partition. The chamber inner cavities are connected via the channel installed in the partition, while the other side walls of the chambers have bumps forming corresponding silphons. The chamber lids are fixed on the interchamber partition via hinges and the vessel for the ferreed sorbent is installed inside the chamber for mixing the ferreed sorbent with the biological fluid and is made in the form of e.g. cylinder with silphon-looking bumped side surface. While one butt-end of the cylinder is fastened to the bottom of the chamber for mixing the ferreed sorbent with the biological fluid, and the other butt-end has a lid fastened in the chamber lid, magnets are installed on the bottom of the chamber for the ferreed sorbent precipitation. The system inlet socket is simultaneously connected with both the mixing chamber inner cavities and the vessel for the ferreed sorbent connected with the mixing chamber inner cavity.

Furthermore, the mixing chamber and the ferreed sorbent precipitation chamber lids are connected or performed either being positioned on one level, or in the form of V-shaped in section profile, and the corps formed by those mixing and precipitation chambers in plane is made e.g. as either a rectangle with round corners, or in the form of circle, or in the form of ellipse, or in the form of figure-of-eight. At those volumes of the ferreed sorbent mixing and precipitation chambers inner cavities are chosen in the proportions of either 1:1, or 1:(0.1-0.9), or (0.1-0.9):1 and correspondingly, a volume of the ferreed sorbent mixing chamber inner cavities and a volume of the ferreed sorbent vessel are chosen in proportion of 1:(0.1-0.9), and the ferreed sorbent vessel is instilled inside the ferreed sorbent mixing chamber at the distance of at least (1-100)d from the side wall of the chamber and at least (10-100)d from the partition between the mixing and the precipitation chambers, where d is an inner diameter of the channel connecting the system inlet socket with the ferreed sorbent mixing chamber inner cavity.

The channel from the inlet socket is input into the ferreed sorbent mixing chamber either through the chamber bottom or through the chamber lid. The channel from the inlet socket is input into the mixing chamber at an angle of (10-80)° to the bottom level, or, correspondingly, to the chamber lid and the vertical line. The channel from the inlet socket is input into the vessel for the ferreed sorbent through the vessel lid or its bottom, and the outlet channel from the ferreed sorbent vessel into the ferreed sorbent mixing chamber is installed e.g. in the lower part of the vessel side wall at the distance of (0.5-50)d from the chamber bottom, where d is the channel diameter.

Furthermore, the channel between the ferreed sorbent mixing and precipitation chambers is installed in the partition between the chambers at the distance of (0.5-50)d from the chambers bottom, where d—channel diameter, and the outlet channel from the ferreed sorbent precipitation chamber is installed in the upper part of the chamber side wall at the distance of (0.5-50)d from the lid, where d—channel diameter.

The magnets are installed either inside of the ferreed sorbent precipitation chamber, or outside of the chamber, or they are installed inside and outside the chamber and are fixed on the bottom of the ferreed sorbent precipitation chamber.

Furthermore, the driving gear for changing volumes of the mixing and precipitation chambers and the vessel is made in the form of e.g. electric motor connected with the lid through e.g. a reduction gear or a tappet gear, or else is made in the form of a reduction gear fixed on the output shaft, e.g. at the angle of (30-45)° to the disc shaft axis. Rotation of the shaft alternatively interacts with chamber lids, or else it is made in the form of tappet gear connected with the lid, operating with the possibility of operator's manual action, or the above driving gear is performed with the operator's manual action directly to the lid.

The spot above the mixing chamber corrugated side wall or the spot above the precipitation chamber corrugated side wall are chosen as the operator's action application spot.

Furthermore, the diameters of input channels going into the ferreed sorbent mixing chamber and the vessel are made in the proportion of $d/di = V/V_b$, where d—inner diameter of the input channel going into the mixing chamber, dj—inner diameter of the input channel going into the vessel, V—mixing chamber, $V_r$—vessel capacity.

Here the walls of the vessel and the mixing and precipitation chambers, as well as the interchamber partitions, the lid and the bottom are made of e.g. polyurethane, and the corrugation is performed at (0.5-0.95) of the respective wall height.

BRIEF DESCRIPTION OF THE DRAWINGS

The biological fluid correction system is shown in.

DETAILED DESCRIPTION OF THE INVENTION

Figure 1:
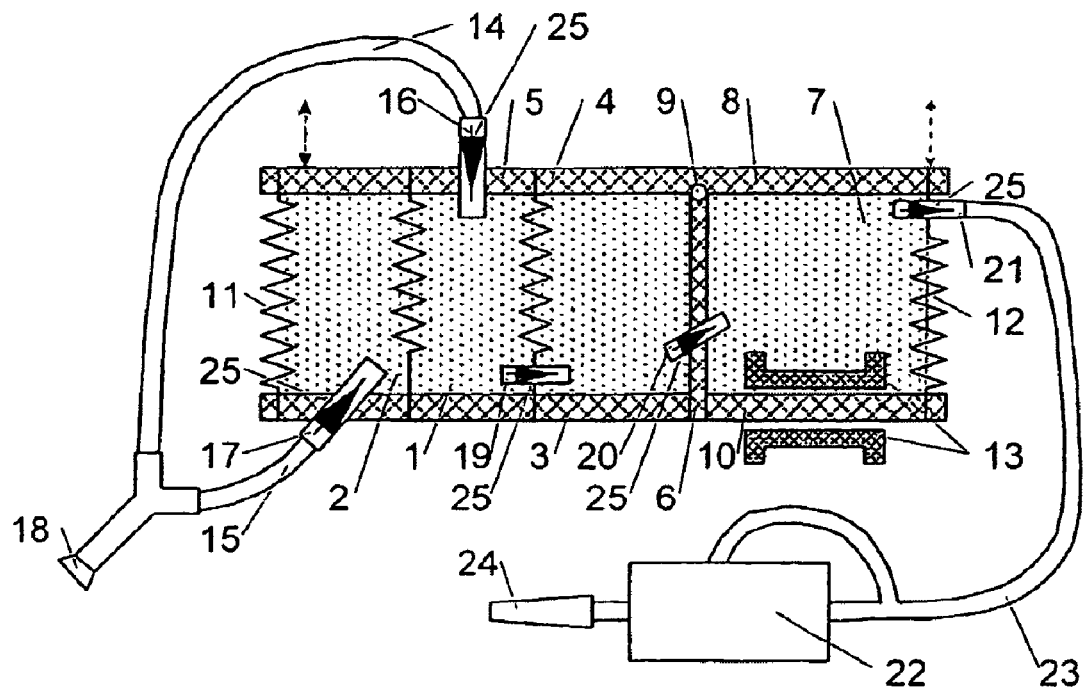
FIG. 1 as a schematic drawing; the system filtering device is shown as a schematic drawing in FIG. 2; the system view with V-shape-connected lids is shown in the FIG. 3; a capacity change driving gear scheme is shown as a schematic drawing in FIG. 4; a system chambers bottom with a hinged fastening device is shown as a schematic drawing in FIG. 5; and variations of the system performance in a plane are shown schematically in the forms of a circle, an ellipse and a figure-eight, respectively, in FIGS. 6-8.

The biological fluid correction system of FIG. 1 includes a vessel 1 for holding the biological fluid intended for purification, e.g. patient's blood out of e.g. ferreed sorbent low-molecular and medium-molecular toxins, not shown in FIG. 1, as discussed in PCT International Application PCT/RU94/00022, performed in the form of a cylindrical silphon, installed in the chamber 2 for mixing of the ferreed sorbent with the biological fluid, designed for providing interaction of the ferreed sorbent with the above fluid. The silphon is performed at cost of part of the cylinder made as respective corrugation ruffles, not numbered on the Figure, and the corrugation is made at (0.5-0.95) of the cylinder surface height. The vessel 1 is fixed on the bottom 3 of the ferreed sorbent mixing chamber 2 with one butt-end (not numbered in the Figure), which has no corrugation alongside. The vessel other butt-end is fixed on the lid 4 of the mixing chamber 2 and hermetically sealed with the lid 5.

Figure 3:
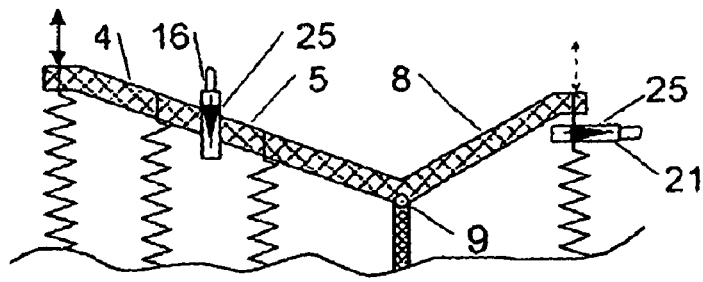
Figure 7:
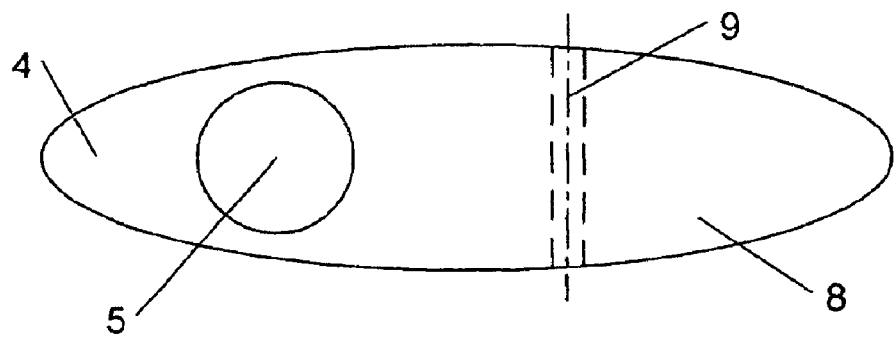

The bottom 3 of the mixing chamber 2 is connected via rigid fastening (FIG. 1) or hinged fastening (FIG. 7) with the wall 6, functioning as a partition between the mixing chamber 2 and the precipitation chamber 7, designed for the ferreed sorbent liberation out of the biological fluid. Here, the lid 4 of the mixing chamber 2 and the lid 8 of the precipitation chamber 7 are rigidly connected among themselves and installed on the wall 6 via the hinge 9 with the ability to swing around it in plane, perpendicular axis (not shown in the Figure) of the hinge. The lids 4 and 8 are placed in either one plane (FIG. 1), or at an angle, e.g. in the form of V in section (FIG. 3), while the lids sizes in the above section (V-shape sides sizes) and, correspondingly, the in-between angle size are chosen in view of providing the requested proportion of capacities of the chambers 2 and 7, and the hinge axis 9 is placed right in the junction of those sides. The bottom 10 of the precipitation chamber 7, and the bottom 3 of the mixing chamber 2, is connected via rigid fastening (FIG. 1) or hinged fastening (FIG. 7) to the wall 6. The outer walls 11 and 12, respectively, of the mixing chamber 2 and the precipitation chamber 7, are formed as corrugated silphons, and here the corrugation in the ferreed sorbent vessel 1, as well as in the chambers 2 and 7 for ferreed sorbent mixing and precipitation, is made at (0.5-0.95) of the respective wall height.

The bottoms 3 and 10, the lids 4, 5 and 8, and the walls 6, 11 and 12 of the chambers 2 and 7 for ferreed sorbent mixing and precipitation respectively, as well as the walls (not numbered in the FIG. 1) of the vessel 1 are made of non-magnetic materials, e.g. of polyurethane.

Magnets 13 are installed in the bottom 10 of the precipitation chamber 7. The magnets 13 are performed as e.g. a permanent magnet from samarium (8 t)-cobalt (Co) alloy, functioning for educing the ferreed sorbent out of the biological fluid. The magnets 13 depending on e.g. design considerations or in order to get the magnetic field of the specified capacity, might be installed either inside of the precipitation chamber 7 under a metal gauze (not shown in the Fig.), or outside on the bottom 10, or both inside and outside the chamber, at that the created by magnets magnetic field capacity should be equal to (10-200) mTl. The example described (FIG. 1) demonstrates one installation of the magnets 13 both inside the chamber 7 on the bottom 10, and outside of the bottom 10 of the precipitation chamber 7.

The vessel 1 for the ferreed sorbent and the mixing chamber 2, constructed as e.g. hose channels 14 and 15 through the socket 16 installed on the lid 5 of the vessel 1 and through the socket 17 installed on the bottom 3 (FIG. 1) or on the lid 4 (not shown in the Fig.) of the mixing chamber 2, respectively, simultaneously are connected to the biological fluid correction system inlet socket 18. Here, the socket 17 is installed with a possibility of input into the mixing chamber 2 at the angle of (10-80) to the bottom 3 level or, respectively, to the lid 5 and e.g. to the wall 6, in order to provide the fluid flow swirling and its better immixture with the ferreed sorbent.

A channel 19, which is designed for the ferreed sorbent transferring into the mixing chamber 2, is made alongside with the side-wall butt-end of the vessel 1, fixed onto the bottom 3 of the mixing chamber 2.

The channel 20 going from the mixing chamber 2 to the precipitation chamber 7 and the channel 21 going from the precipitation chamber 7 to the filtering device 22, respectively, are installed by placing the channel 20 in the interchamber partition or wall 6 alongside to its junction with the bottom 3 of the mixing chamber 2 at the angle of (10-60) to the bottom 10 of the precipitation chamber 7 and to the wall 6. The channel 21 is placed in the upper wall 12 of the precipitation chamber 7. The filtering device 22 is connected with the system outlet socket 24 via the channel 23.

In order to provide directed flow of the biological fluid from the inlet socket 18 through the system to the outlet socket 24, the reverse valves 25 are installed in the system channels.

Figure 2:
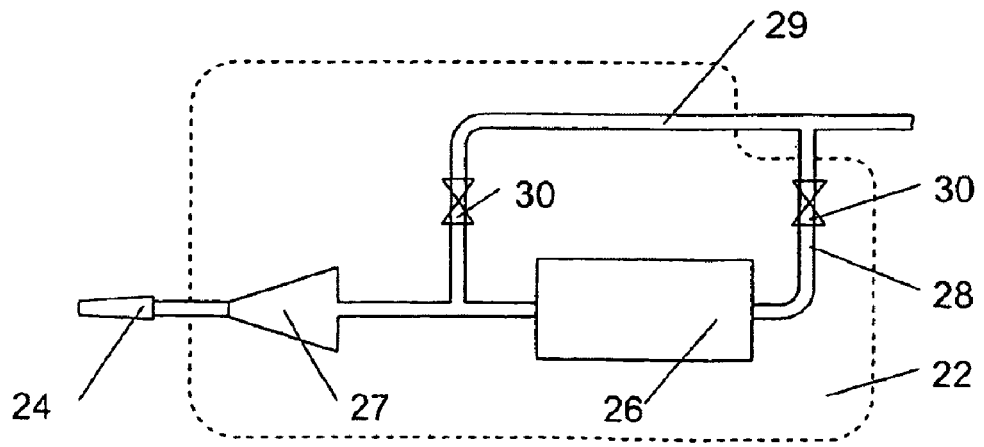

The filtering device 22 is performed (FIG. 2) in the form of the respective device, such as taught by U.S. Pat. No. 5,980,479, including a sequentially installed ultra-filterer 26 and trap 27 (refer to the above), designed for cleansing the biological fluid out of any therein mixed foreign/extraneous liquids, e.g. water drops or air bubbles. Faucets 30 are installed on the ultra-filter inlet and bypass channels 28 and 29. Correspondingly, the faucets can ensure the possibility of the ultra-filter 26 activation and its inclusion to the biological fluid correction system operation, as well as its respective deactivation. Here, the bypass channel 29 is included for providing the system operation in the mode of deactivated ultra-filter 26.

The capacities of the inner cavities of the mixing chamber 2 and the precipitation chamber 7 are designed in proportions of either 1:1, or 1:(0.1-0.9), or (0.1-0.9):1 and respectively, capacities of the inner cavities of the mixing chamber 2 and the vessel 1 are designed in the proportions of 1:(0.1-0.9), and, the vessel 1 is installed in the mixing chamber 2 at the distance of at least (1-100)d from the side wall 11 of the above chamber and at least (10-100)d from the interchamber partition 6, where d—the inner diameter of the channel 15 connecting the system inlet socket 18 with the inner cavity of the mixing chamber 2. In the example described above d=(5-15) mm.

At that the inner diameters of the inlet channels 15 and 14 (going into the mixing chamber 2 and the vessel 1, respectively) are designed in the proportion of $d/di=V/V_b$, where d—the inner diameter of the channel 15 going into the mixing chamber 2; di—inner diameter of the channel 14 going into the vessel 1; V—the mixing chamber 2 capacity; Vp—vessel 1 capacity. In the example described above Vi=(5-50) ml.

Furthermore, the output channel 19 going from the vessel 1 into the mixing chamber 2, is installed e.g. in the lower part of the vessel side wall at the distance of (0.5-50)d from the bottom of the chamber, where d—diameter of the channel 19; while the channel 20 between the mixing chamber 2 and the precipitation chamber 7 is installed in the partition 6 between those chambers at the distance of (0.5-50)d from the bottom 3 of the mixing chamber 2 at an angle of (10-60)° to the planes of the wall 6 and the bottom 10, where d—inner diameter of the channel 20; and the outer channel 21 going from the precipitation chamber 7 is installed in the upper part of the side wall 12 of the precipitation chamber 7 at the distance of (0.5-50)d from the lid 8, where d—inner diameter of the channel 21. In the example described above, diameters of the channels 15, 19, 20, 21, 23, 28 and 29 are designed equal.

The driving gear (not shown in the Fig.) for changing capacities of the chambers 2 and 7, and the vessel 1, is made in the form of e.g. electric motor (not shown in the Fig.), connected with the lid 4 or 8, e.g. through a reducing gear with a tappet mechanism (not shown in the Fig.), or in the form of a disc 31, fixed on the reducing gear output shaft (not shown in the Fig.), e.g. at the angle of (30-45)° to the shaft axe (FIG. 4), at the shaft rotation alternatively interacting with the chamber lids, or else in the form of a tappet mechanism connected with the lid (not shown in the Fig.), operating with the possibility of operator's manual action, or the above driving gear is made with the possibility of operator's manual action directly to the lid.

Figure 4:
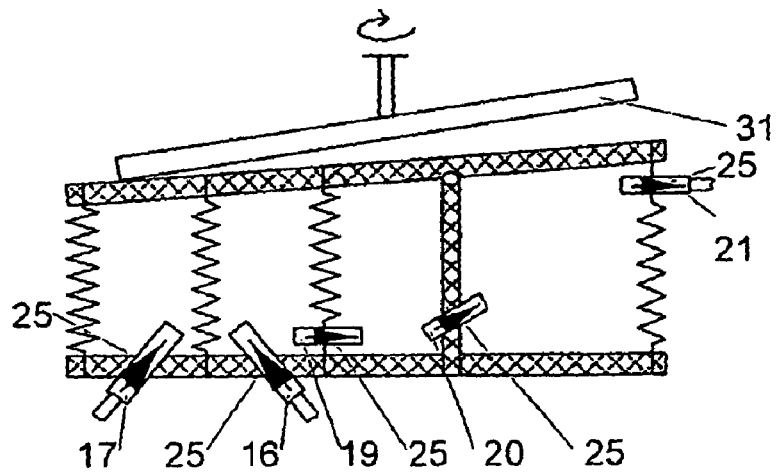

The spot above the mixing chamber 2 corrugated side wall 11 or the spot above the precipitation chamber 7 corrugated side wall 12 are chosen as the operator's action application spot (FIGS. 1 and 4).

Figure 5:
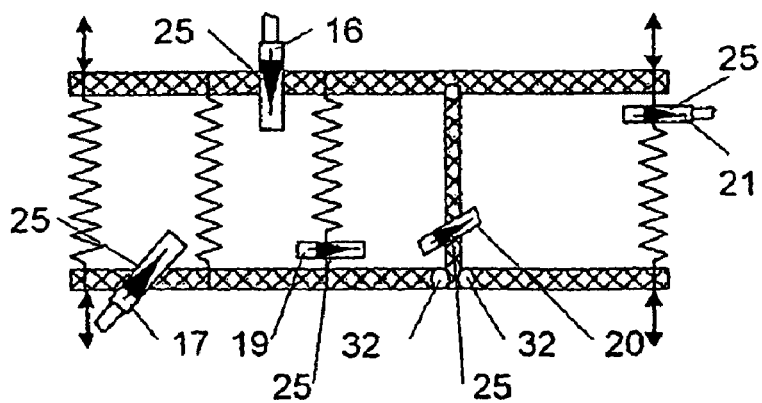

Furthermore, in the case of constructive performance of the bottom 3 of the mixing chamber 2 and of the bottom 10 of the precipitation chamber 7 with the capacity of rotation, the above bottoms are fixed on the interchamber partition (wall 6) via the hinges 32 (FIG. 5), providing the possibility of each bottom rotation in the respective chamber lid rotation plane. In order to avoid a non-sanctioned turn of the bottom, the hinges 32 are equipped with locking screws (not shown in the Fig.).

Figure 6:
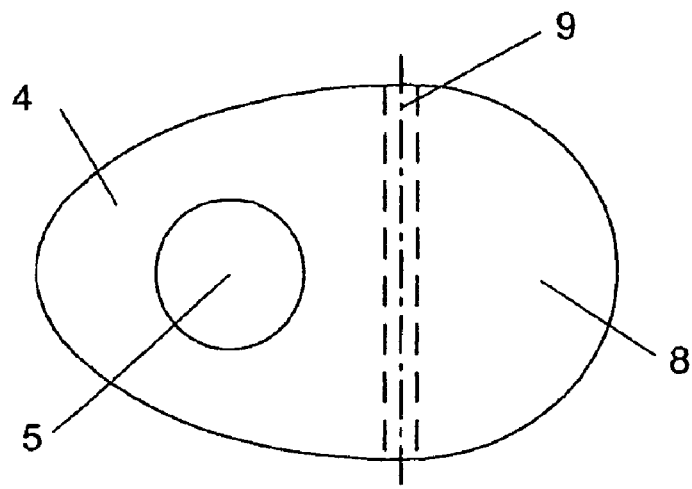
Figure 8:
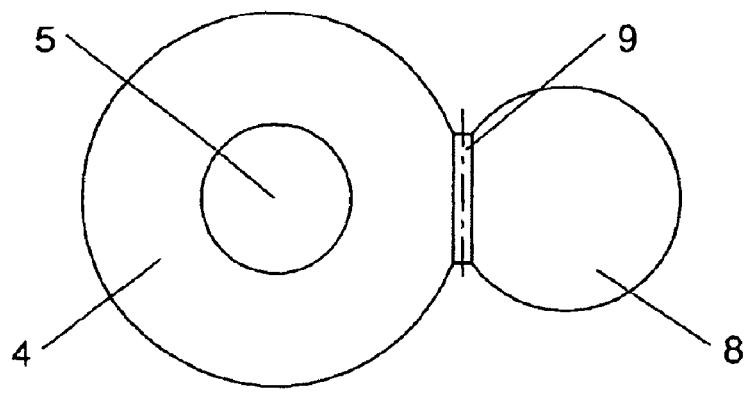

Configuration of the corps formed by the mixing chamber 2 and the precipitation chamber 7, in a plane, can be performed in the form of e.g. either rectangular shape with rounded corners, (not shown in the Fig.), or as a circle (FIG. 6), or as an ellipse (FIG. 7), or as a figure-of-eight (FIG. 8).

The biological fluid correction system operates in the following manner.

Periodical, with the frequency depending on e.g. rotational speed of the disc 31, or on the frequency of pressing the lid by e.g. operator, rotational action of the driving gear to the lids 4 and 8, respectively, of the mixing chamber 2 and the precipitation chamber 7, changes capacities of the above chambers with the same frequency, as well as changes a capacity of the vessel 1 placed in the inner cavity of the mixing chamber 2. Such change of capacities, correspondingly, changes pressure inside the chambers and the vessel, increases it at capacity reduction, and reduces at capacity increase, and thus the respective biological fluid is periodically soaked into the correction system, which is connected with e.g. patient's blood-vascular system, or just with a reservoir containing a biological fluid (not shown in the Fig.), and is output after being corrected, correspondingly into the patient's blood-vascular system or into a special reservoir.

Here the biological fluid, e.g. blood from the patient's vein, simultaneously gets into the vessel 1 which is preliminarily filled up with the ferreed sorbent, and into the mixing chamber 2 through the respective channels due to the driving gear action directed to increase the vessel 1 and the mixing chamber 2 capacities, in the amount proportional to the respective capacity change value. The blood getting into the vessel 1 makes a respective suspension with the ferreed sorbent already sitting in the vessel, and then the above suspension amount commensurable to the value of the vessel capacity reduction resulting from the driving gear action, gets into the mixing chamber 2 through the channel 19, where the ferreed sorbent of the above suspension is mixed and interacts with the blood preliminarily entered into the chamber, while absorbing respective toxic impurities, as taught by PCT International Application PCT/RU94/00022. The entering biological fluid flow/jet swirl, due to the blood input under the above mentioned angle with respect to the mixing chamber bottom 3 and the walls 6 and 11, expedites intensive immixture of the above blood with the ferreed sorbent in the mixing chamber 2. The part of the biological fluid which enters into the vessel 1 for composing a suspension with the ferreed sorbent, does also interact with the above sorbent, however, the concentration of the sorbent in the suspension, as well as the treating capacity of the above sorbent connected with its amount, significantly exceeds any losses for that interaction process.

At the mixing chamber 2 capacity reduction and the respective increase of the capacity of the precipitation chamber 7, the purified blood suspension with the ferreed sorbent goes through the channel 20 into the precipitation chamber 7, where the ferreed sorbent is precipitated under the influence of a magnet field in the zone of placement of magnets 13, and the purified blood at the following reduction of the chamber 7 capacity goes through the channel 21 into the filtering device 22, after going thorough the filtering device 22, the blood can be respectively injected into the patients blood-vascular system.

If the system pressure is not sufficient for biological fluid running through the filtering device 22, e.g. a pump of e.g. peristaltic type e.g. installed in the system output channel 23 can be used as well (not shown in the Fig.).

INDUSTRIAL APPLICABILITY

The proposed performance of the biological fluid correction system provides the possibility of biological fluids quality purification without using any additional reagents, e.g. through using the ferreed sorbent with no physiological solution, and it allows to significantly minimize the system dimensions without any decrease of useful capacities of both chambers and the vessel. It also allows to simplify the construction factually providing the possibility to make disposable systems, that enables using the propose biological fluids correction system not only in clinical conditions, but also in conditions of ambulance and emergency, e.g. in emergency/disaster medicine.

The invention claimed is:

1. A system including hermetic parts connected via channels with valves installed in the channels for providing flow of a biological fluid through the system from an inlet socket to an outlet socket, the system comprising:
   a vessel for a ferreed sorbent,
   a mixing chamber for mixing the ferreed sorbent with the biological fluid;
   a precipitation chamber for precipitation of the ferreed sorbent out of the biological fluid;
   magnets installed on a bottom of the precipitation chamber;
   a filtering device connected with an outlet channel of the precipitation chamber;
   the filtering device, the outlet socket, the mixing chamber, the precipitation chamber and the vessel for the ferreed sorbent having variable capacities;
   the mixing chamber and the precipitation chamber formed as vessels having one of hard-jointed lids or a mutual lid, a mutual wall fixed to bottoms of the chambers, a mutual wall forming an interchamber partition, inner cavities of the chambers connected through a channel in the interchamber partition, and other side walls of the chambers having corrugations forming corresponding silphons, wherein the chamber lids are fixed on the interchamber partition via hinges with a possibility to rotate around a hinge axis and the biological fluid flows from the mixing chamber to the precipitation through the channel in the interchamber partition;
   wherein the vessel for the ferreed sorbent is installed inside the mixing chamber and an inner cavity of the vessel connected with an inner cavity of the mixing chamber, and the vessel is formed as a cylinder with a silphon-type corrugated side wall surface with a first butt-end of the cylinder fixed on the bottom of the mixing chamber and a second butt-end of the cylinder having a lid fixed on the mixing chamber lid; and
   the system inlet socket simultaneously connected to the inner cavity of each of the mixing chamber and the vessel for the ferreed sorbent.

2. The system of claim 1 wherein the lids of the mixing chamber and the precipitation chamber are located in one plane.

3. The system of claim 1 wherein the lids of the mixing chamber and the precipitation chamber are connected in a form of an angle-shape.

4. The system of claim 3 wherein a shape formed by the mixing chamber and the precipitation chamber in a plane is in a form of one of a rectangle with rounded corners, a circle, an ellipse, and a figure-eight shape.

5. The system of claim 3 wherein the bottoms of the chambers for the ferreed sorbent mixing and precipitation are hard-fixed on the interchamber partition.

6. The system of claim 3 wherein the bottoms of the chambers for the ferreed sorbent mixing and precipitation are fixed on the interchamber partition are rotatable in a lid rotation plane.

7. The system of claim 3 wherein capacities of inner cavities of the chambers for the ferreed sorbent mixing and precipitation are in a proportion of one of 1:1, 1:(0.1-0.9), and (0.1-0.9):1 and capacities of inner cavities of the mixing chamber and the vessel are in a second proportion of 1:(0.1-0.9).

8. The system of claim 1, wherein the vessel for ferreed sorbent is installed inside the mixing chamber at a distance of at least (1-100)d from the side wall of the above chamber and at least (10-100)d from the interchamber partition, where d is an inner diameter of the channel connecting the inlet socket with the inner cavity of the mixing chamber.

9. The system of claim 8 wherein the channel from the inlet socket is input into the mixing chamber through one of the chamber bottom and the lid.

10. The system of claim 9 wherein the channel from the inlet socket is input into the mixing chamber at an angle of (10-80)° to a bottom plane and, respectively, to the chamber lid and a vertical line.

11. The system of claim 8 wherein the channel from the inlet socket is input into the vessel through the vessel lid, and the output channel going from the vessel to the mixing chamber is installed in the vessel and the mixing chamber side walls at the distance of (0.5-50)d from the mixing chamber bottom, where d is the channel diameter.

12. The system of claim 8 wherein the channel between the chambers for the ferreed sorbent mixing and precipitation is installed in the interchamber partition at a distance of (0.5-50)d from the chambers bottoms, where d is a channel diameter.

13. The system of claim 8 wherein the channel between the chambers for the ferreed sorbent mixing and precipitation is installed in the interchamber partition at the angle of (10-60)° to the bottom of precipitation chamber and the interchamber partition.

14. The system of claim 8 wherein the output channel from the precipitation chamber is installed in one of the chamber lid and an upper part of the chamber side wall at a distance of (0.5-50)d from the lid, where d is a channel diameter.

15. The system of claim 8, wherein diameters of input channels going into the mixing chamber and the vessel are chosen in a proportion of $d/d1=V/V_1$, where d is an inner diameter of the channel going into the mixing chamber, d1 is an inner diameter of the channel going into the vessel, V is a mixing chamber capacity, and $V_1$ is a vessel capacity.

16. The system of claim 1 wherein magnets are installed at least one of inside the precipitation chamber, outside of the above chamber, and both inside and outside the precipitation chamber, and are fixed on the bottom of the above chamber.

17. The system of claim 1 wherein the walls of the vessel, the mixing chamber and the precipitation chamber and the partition between the above chambers, as well as the lid and the bottom are made of polyurethane.

18. The system according to claim 17, wherein the corrugation in the vessel and the chambers for the ferreed sorbent mixing and precipitation is made at (0.5-0.95) of a height of a respective wall.

19. The system of claim 1 wherein a shape formed by the mixing chamber and the precipitation chamber in a plane is in a form of one of a rectangle with rounded corners, a circle, an ellipse, and a figure-eight shape.

20. The system of claim 1 wherein the bottoms of the chambers for the ferreed sorbent mixing and precipitation are hard-fixed on the interchamber partition.

21. The system of claim 1 wherein the bottoms of the chambers for the ferreed sorbent mixing and precipitation are fixed on the interchamber partition and are rotatable in a lid rotation plane.

22. The system of claim 1 wherein capacities of inner cavities of the chambers for the ferreed sorbent mixing and precipitation are in a proportion of one of 1:1, 1:(0.1-0.9), and (0.1-0.9):1 and capacities of inner cavities of the mixing chamber and the vessel are in a second proportion of 1:(0.1-0.9).

23. The system of claim 1 wherein the channel from the inlet socket is input into the mixing chamber through one of the chamber bottom and the lid.

24. The system of claim 23 wherein the channel from the inlet socket is input into the mixing chamber at an angle of (10-80)° to a bottom plane and, respectively, to the chamber lid and a vertical line.

25. The system of claim 1 wherein the channel from the inlet socket is input into the vessel through the vessel lid, and the output channel going from the vessel to the mixing chamber is installed in the vessel and the mixing chamber side walls at the distance of (0.5-50)d from the mixing chamber bottom, where d is the channel diameter.

26. The system of claim 1 wherein the channel between the chambers for the ferreed sorbent mixing and precipitation is installed in the interchamber partition at a distance of (0.5-50)d from the chambers bottoms, where d is a channel diameter.

27. The system of claim 1 wherein the channel between the chambers for the ferreed sorbent mixing and precipitation is installed in the interchamber partition at the angle of (10-60)° to the bottom of precipitation chamber and the interchamber partition.

28. The system of claim 1 wherein the output channel from the precipitation chamber is installed in one of the chamber lid and an upper part of the chamber side wall at a distance of (0.5-50)d from the lid, where d is a channel diameter.

29. The system of claim 1 wherein a spot one of above the mixing chamber corrugated side wall and above the precipitation chamber corrugated side wall is a driving gear application spot.

30. The system of claim 1, wherein diameters of input channels going into the mixing chamber and the vessel are chosen in a proportion of $d/d1=V/V_1$, where d is an inner diameter of the channel going into the mixing chamber, d1 is an inner diameter of the channel going into the vessel, V is a mixing chamber capacity, and $V_1$ is a vessel capacity.

31. The system of claim 1 wherein the corrugation in the vessel and the chambers for the ferreed sorbent mixing and precipitation is made at (0.5-0.95) of a height of a respective wall.

* * * * *